(12) United States Patent
Crisman et al.

(10) Patent No.: US 12,082,842 B2
(45) Date of Patent: Sep. 10, 2024

(54) ECHOGENIC NEEDLE ASSEMBLIES AND METHOD OF USE THEREOF

(71) Applicant: SMITHS MEDICAL INTERNATIONAL LIMITED, Kent (GB)

(72) Inventors: Andrew Crisman, Shoreview, MN (US); Stephen James Field, Kent (GB); Alysa Lauren Granata, Minneapolis, MN (US); Neil Adam Tookman, Middlesex (GB)

(73) Assignee: Smiths Medical International Limited, Ashford (GB)

( * ) Notice: Subject to any disclaimer, the term of this patent is extended or adjusted under 35 U.S.C. 154(b) by 652 days.

(21) Appl. No.: 15/297,767

(22) Filed: Oct. 19, 2016

(65) Prior Publication Data

US 2017/0112528 A1    Apr. 27, 2017

Related U.S. Application Data

(60) Provisional application No. 62/246,222, filed on Oct. 26, 2015.

(51) Int. Cl.
| | | |
|---|---|---|
| *A61B 17/34* | (2006.01) | |
| *A61B 8/08* | (2006.01) | |
| *A61B 90/00* | (2016.01) | |

(52) U.S. Cl.
CPC ........ *A61B 17/3403* (2013.01); *A61B 8/0841* (2013.01); *A61B 17/3415* (2013.01); (Continued)

(58) Field of Classification Search
CPC ............ A61B 17/3403; A61B 17/3417; A61B 17/3415; A61B 17/3423; A61B 8/0841; (Continued)

(56) References Cited

U.S. PATENT DOCUMENTS 4,419,095 A * 12/1983 Nebergall ......... A61M 25/1027
                                                   128/207.15
5,024,659 A *  6/1991 Sjostrom ............ A61M 25/065
                                                        604/110
(Continued)

FOREIGN PATENT DOCUMENTS

JP        2006101915 A       4/2006
JP        2010194013 A  *    9/2010
(Continued)

OTHER PUBLICATIONS

JP 2010194013 A (Hoya Corp). Translated by Espacenet. Sep. 9, 2010 [retrieved on Sep. 30, 2019]. (Year: 2010).*
(Continued)

*Primary Examiner* — Sean D Mattson
(74) *Attorney, Agent, or Firm* — Louis Woo

(57) ABSTRACT

A needle assembly has a needle having an echogenic feature proximate to its distal sharp tip mounted to an echogenic cannula, with the echogenic tip of the needle extending beyond the distal end of the cannula. The echogenic tip provides guidance for the movement of the needle assembly under ultrasound observation so that the needle assembly may be more readily maneuvered inside a body. Once correctly positioned, the needle is removed and further confirmation may be made under ultrasound observation that the cannula has been correctly positioned inside the body. The echogenic feature of the needle may be at least one spiral groove that is tilted at an angle relative to the tip of the needle to effect a substantially 180° reflection of the ultrasound. An alternative echogenic feature to improve reflected echogeneity has crisscrossing grooves each having a predetermined pitch density formed at a neutral position on the needle.

12 Claims, 5 Drawing Sheets

(52) U.S. Cl.
CPC ...... *A61B 17/3417* (2013.01); *A61B 17/3423* (2013.01); *A61B 2017/3413* (2013.01); *A61B 90/39* (2016.02); *A61B 2090/3925* (2016.02)

(58) Field of Classification Search
CPC ............ A61B 2090/3925; A61B 90/39; A61B 2017/3413
USPC ........................................................ 600/437
See application file for complete search history.

(56) References Cited

U.S. PATENT DOCUMENTS

| | | | | |
|---|---|---|---|---|
| 5,383,466 | A * | 1/1995 | Partika | A61B 17/3403 600/459 |
| 5,490,521 | A * | 2/1996 | Davis | A61B 8/0833 600/458 |
| 5,718,676 | A | 2/1998 | Barrett | |
| 5,759,154 | A | 6/1998 | Hoyns | |
| 5,766,135 | A * | 6/1998 | Terwilliger | A61B 8/0833 600/562 |
| 6,053,870 | A * | 4/2000 | Fulton, III | A61B 17/3421 600/458 |
| 8,092,390 | B2 * | 1/2012 | Field | A61B 17/435 600/458 |
| 8,617,079 | B2 | 12/2013 | Mitchell | |
| 2003/0065266 | A1 | 4/2003 | Russell | |
| 2004/0059296 | A1 * | 3/2004 | Godfrey | A61M 25/0668 604/164.05 |
| 2009/0005774 | A1 * | 1/2009 | Fernald | A61L 31/18 606/41 |
| 2009/0131734 | A1 * | 5/2009 | Neustadter | A61N 5/1049 600/8 |
| 2010/0160731 | A1 * | 6/2010 | Giovannini | A61B 17/3478 600/117 |
| 2010/0256577 | A1 * | 10/2010 | Field | A61B 17/3403 604/272 |
| 2010/0317963 | A1 * | 12/2010 | Clancy | A61F 2/95 600/424 |
| 2012/0101380 | A1 | 4/2012 | Blum et al. | |
| 2012/0253297 | A1 * | 10/2012 | Matsuzawa | A61M 5/158 604/272 |
| 2013/0225997 | A1 | 9/2013 | Dillard et al. | |
| 2013/0267942 | A1 | 10/2013 | Fulton, III | |
| 2014/0128823 | A1 * | 5/2014 | Odland | A61B 5/150213 604/319 |
| 2014/0276073 | A1 * | 9/2014 | Quearry | A61B 8/4455 600/458 |
| 2014/0336687 | A1 * | 11/2014 | Iwase | B24B 19/028 451/28 |
| 2015/0012008 | A1 | 1/2015 | McWeeney | |
| 2016/0120509 | A1 * | 5/2016 | Syed | A61B 8/481 600/424 |

FOREIGN PATENT DOCUMENTS

| | | | |
|---|---|---|---|
| WO | WO-02078611 A2 * | 10/2002 | ........... A61K 9/5089 |
| WO | WO 2014/080153 A1 | 5/2014 | |
| WO | WO 2015/008014 A1 | 2/2015 | |

OTHER PUBLICATIONS

PCT International Search Report and Written Opinion of the ISA/EP, corresponding PCT Application No. PCT/IB2016/001503), mailed Jan. 9, 2017.

* cited by examiner

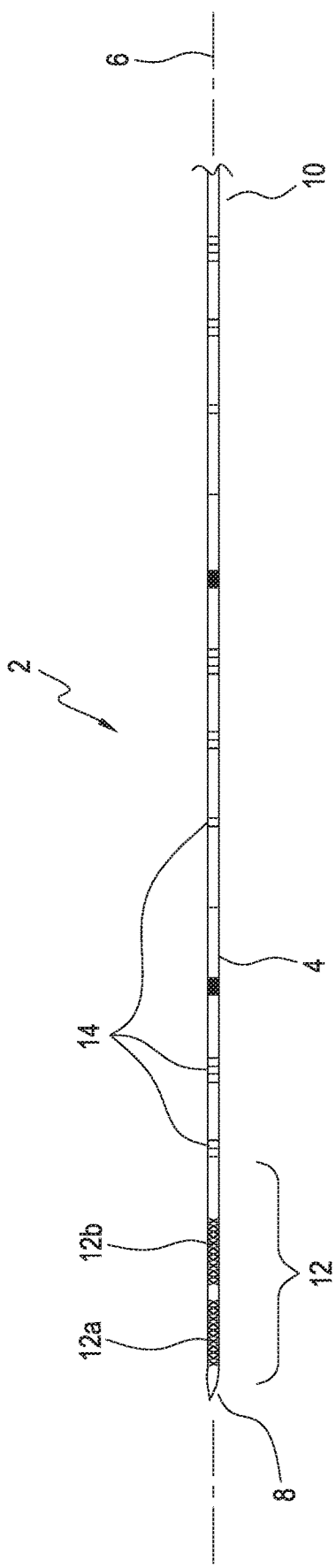
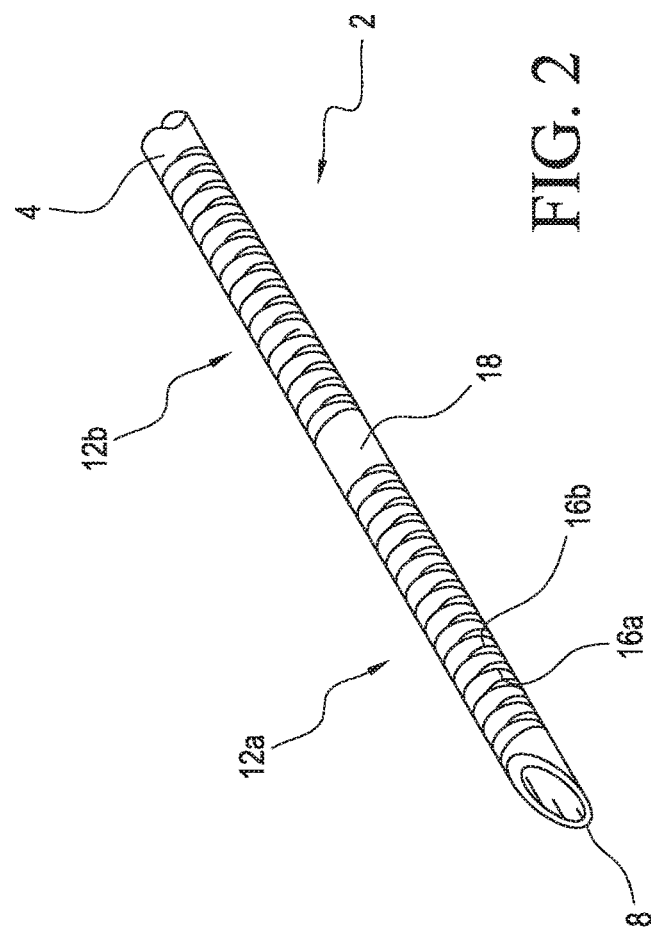

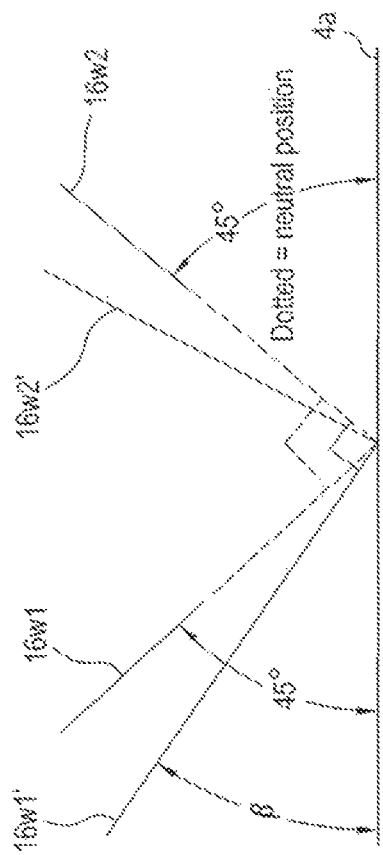
FIG. 3
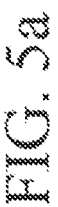
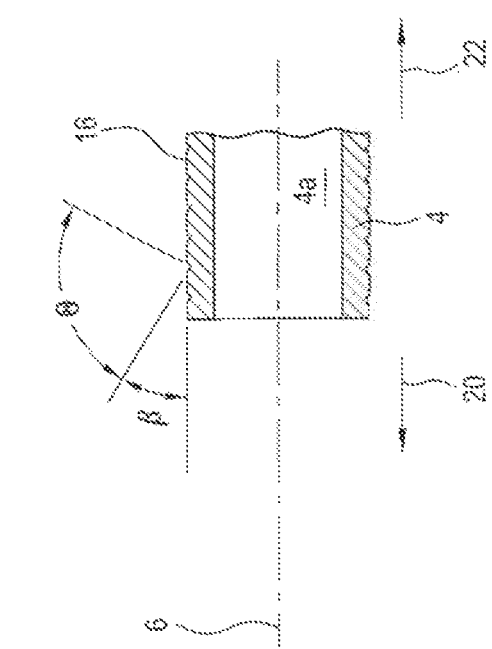
FIG. 4
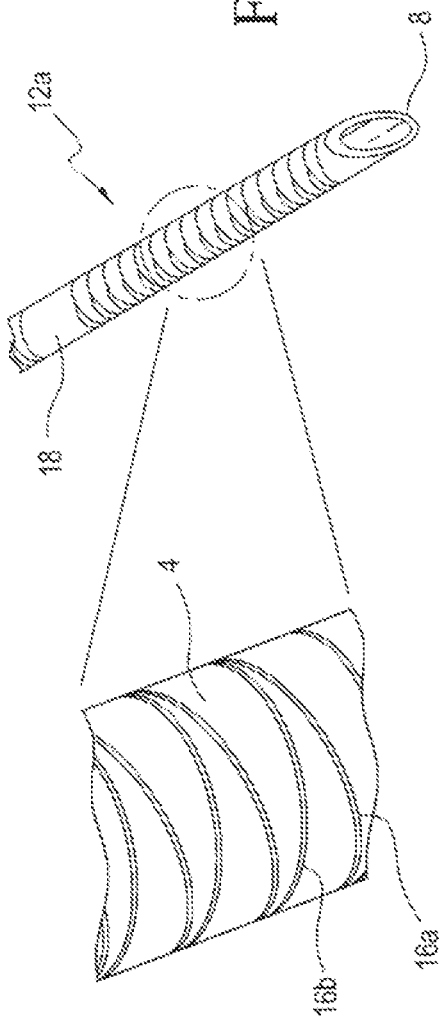
FIG. 5a
FIG. 5b

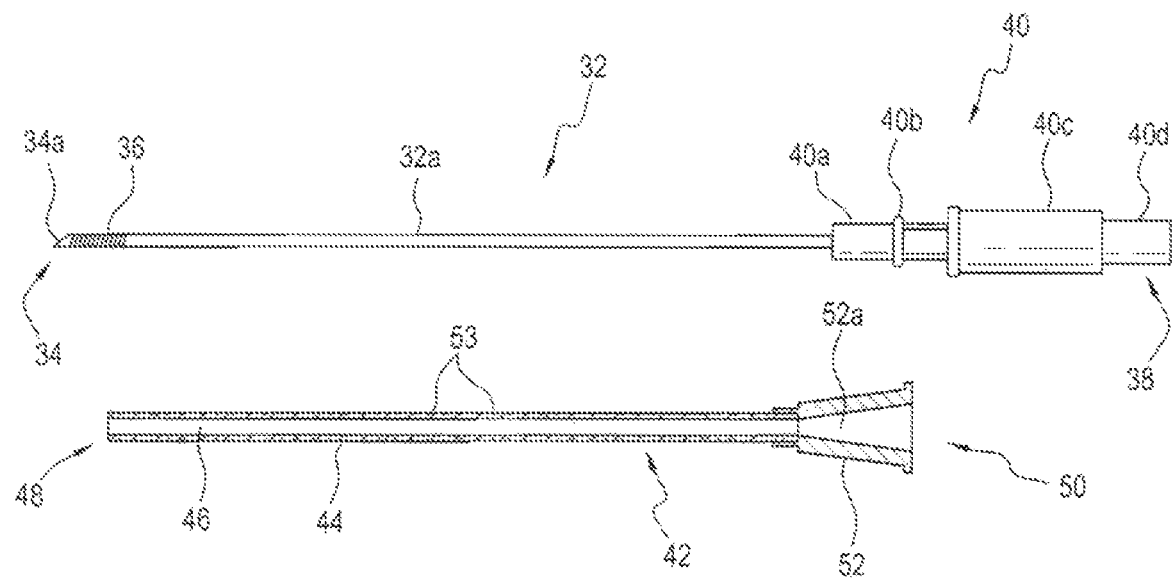
FIG. 8
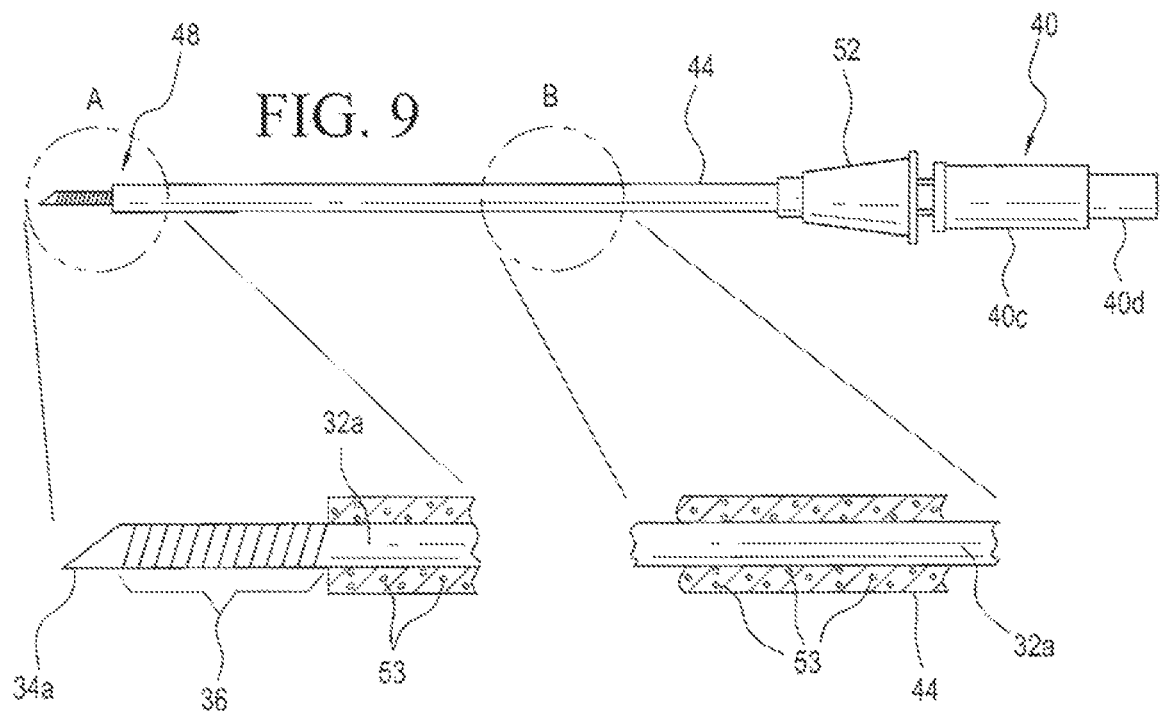
FIG. 9
FIG. 10A   FIG. 10B

US 12,082,842 B2

ECHOGENIC NEEDLE ASSEMBLIES AND METHOD OF USE THEREOF

FIELD OF THE INVENTION

The present invention relates to echogenic medical devices, and more particularly an echogenic needle assembly that may be used to more accurately place and position a cannula into a body.

BACKGROUND OF THE INVENTION

Ultrasound scanners are used increasingly to help direct or check placement of catheters and other devices inserted in the body. Some of these devices are not normally very visible under ultrasound because of their shape, size or the fact that the material from which they are made has similar reflectance acoustic impedance to the tissue or body fluid within which they are inserted. Attempts have been made to increase the visibility of medico-surgical devices under ultrasound observation in various ways. Where the device, such as a needle, is of a metal, the usual way of increasing its visibility is by modifying its surface, such as by forming grooves or indentations in its surface. One such echogenic needle known is the Wallace Amniocentesis Needle(s) that is being sold by the assignee of the instant invention. Other methods of making echogenic needles include applying a reflective coating to the device, such as incorporating bubbles, as described in WO98/19713 and EP0624342. Where the device is of a plastics material, such as a catheter of the kind described in GB2379610, the wall may include gas bubbles or a bubble-containing material may be incorporated in a stripe occupying only a part of the circumference. GB2400804 describes a similar catheter with several layers. U.S. Pat. No. 7,258,669 describes a catheter with a helical, gas-filled lumen extending along its length. DE 102006051978 describes a bubble-filled rod inserted along the bore of a flexible plastics catheter to enhance visibility under ultrasound observation. U.S. Pat. No. 8,398,596, assigned to the assignee of the instant application, discloses a bubble-filled stylet rod inserted along the bore of a needle, as well as disclosing an ultrasound visible sleeve that extend along the outside of a needle.

Embodiments of the instant application are directed to improvements to the echogenic features of needles used in different surgical procedures including peripheral nerve block (PNB), epidural and others that require radiographic or ultrasound observation of the needle during the procedure.

Also disclosed in the instant application is a needle assembly that combines an echogenic needle, including any of the above disclosed enhanced echogenic needle embodiments, with an echogenic cannula so that the needle assembly thus formed is adapted to be readily guided during its placement into the body of a subject patient under ultrasound observation, and the positioning of the cannula in the body after the placement can readily be confirmed.

SUMMARY OF THE PRESENT INVENTION

A first embodiment of an echogenic needle of the instant invention has at its distal portion adjacent its patient end at least one section that has a spiral V-shaped groove. The walls of the groove are orthogonal to each other. The groove is tilted at a given angle from its neutral position toward the proximal end of the needle. The embodiment needle is usually inserted into a subject patient at a desirable insertion angle. If the needle is under ultrasound imaging whereby an ultrasound wave is directed to the needle, at least one wall of the tilted groove would reflect the ultrasound wave back to the receiver of the transducer at substantially the reverse direction, i.e., at approximately 180°, to present an improved ultrasound image of the echogenic needle.

By forming the echogenic groove in a spiral fashion, while maintaining the preferred tilt angle to the groove, the echogenic needle of the instant invention may be made simply. Moreover, that the walls of the groove are orthogonal to each other means that the only angle that needs to be adjusted with regard to the production of the echogenic needle is the tilt angle, which may simply be done by adjusting either the angle of the needle shaft that is being cut, or the angle of the cutting wheel or tool used to cut the groove as the needle shaft is rotatably moved relative to the cutting wheel, which may also be rotating.

Instead of one spiral groove, the echogenic section of the needle may be made with two crisscrossing spiral grooves, i.e., one clockwise and one counter-clockwise relative to the sharp tip of the needle. Each of the V-shaped grooves has walls that are orthogonal to each other. Furthermore, the grooves each may be orientated or tilted at a predetermined angle relative to the proximal end of the needle to effect a substantially 180° reflection of the ultrasound wave from the transducer back to the transducer, when the needle is positioned at an insertion angle that facilitates the insertion of the needle into the subject patient.

A second embodiment of the needle of the invention has a spiral groove that does not have a tilt angle. Instead, the pitch between the tips of the walls of the V-shaped groove is decreased so that the number of turns for a given distance of the groove increases. It was determined that as a result of the increased pitch density, an enhanced ultrasound wave is reflected back to the receiver of the transducer to provide an improved image of the echogenic needle without the need to tilt the groove from its neutral position as is done in the first needle embodiment. Thus, for the second needle embodiment, the pitch of the groove is decreased such that the pitch density for the spiral groove is increased to a range that leads to an improved reflection of the ultrasound image without the need to tilt the groove.

As in the first needle embodiment, instead of one spiral groove, the echogenic section of the needle may have two crisscrossing spiral grooves, one having a clockwise rotation and the other having a counterclockwise rotation relative to the sharp tip of the needle. Since there is no tilting, the walls of the V-shaped grooves, in addition to being substantially orthogonal to each other, would have the same length or height from the bottom to the top of the walls, i.e., the lowest point or the valley in the groove to the uppermost tip or the apex of the V-shaped groove.

Instead of one echogenic section, the distal portion of the needle shaft may have a plurality of echogenic sections. For the exemplar needle embodiments, the needle shaft has two echogenic sections separated by a non-groove section, so that there are two sections of crisscrossing spiral grooves. As discussed above, each groove is adapted to either tilted at a predetermine angle, or remain at its neutral position relative to the longitudinal axis of the needle but has an increased pitch density.

The needle of the instant invention for viewing under ultrasound imaging therefore may comprise a shaft extending along a longitudinal axis having a proximal end and a distal end including a sharp tip, one and other grooves spirally formed clockwise and counterclockwise, respectively, from at least adjacent the sharp tip along a distal portion of the shaft so that the one and other grooves crisscross each other a predetermined distance along the distal portion, the one and other grooves each being at a neutral position relative to the longitudinal axis of the shaft, each of the one and other grooves has an increased pitch density in a range that enhances the reflection of the ultrasound wave from an ultrasound transducer directed to the shaft as an improved reflection image back to the transducer. The walls of each of the grooves are orthogonal to each other and have the same length.

Further disclosed herein is an echogenic needle assembly that combines an echogenic needle, including a needle with the echogenic features as described above, with an echogenic cannula to improve the accessing of a particular portion in a body, for example a blood vessel in a subject patient, and also to confirm that the cannula is correctly positioned in the body after the removal of the needle. Such echogenic needle assembly may be used for central venous catheter (CVC) procedure, epidural and other procedures that require the placement of a cannula or catheter in a subject patient, as well as possibly for percutaneous procedures whereby a tube is inserted into the trachea of the patient. To that end, an echogenic needle, for example either of the above described needle embodiments, is fittingly inserted into an echogenic cannula that may be either plastic or metal. The cannula is made echogenic by for example having gas bubbles or other gas interstices formed in the body of the cannula. The cannula and the needle have cooperating hubs, so that when the cannula and the needle are fully mounted to each other, the cannula and needle hubs are frictionally engaged to each other and the tip of the needle, which has the echogenic feature, extends beyond the distal end of the cannula. The echogenic tip may be used, under ultrasound observation, to guide the movement of the needle assembly into the body of the subject patient, so that the needle assembly may be moved to the desired location in the body, for example the appropriate blood vessel, to which the distal end of the cannula is to be located.

Upon the initial location of the desired location such as the appropriate blood vessel in the body of the subject patient with the echogenic tip of the needle, with the distal end of the cannula having been guided into the blood vessel, the needle is removed. Since the cannula is echogenic, whether the cannula has been correctly positioned within the body can further be confirmed under ultrasound.

Thus, the instant invention is directed to a method of confirming correct placement of a cannula in a body, comprising the steps of mounting an echogenic cannula with a needle having a sharp tip and at least an echogenic feature at or proximate to the tip; inserting the tip of the needle into the body; confirming the proper insertion of the tip of the needle in the body with an ultrasound instrument; confirming the placement of the cannula in the body with the ultrasound instrument; and removing the needle to leave the cannula in place.

The instant invention is further directed to a needle assembly, comprising: an echogenic cannula longitudinally mounted with a needle having a sharp tip with an echogenic feature at or proximate to the tip, the tip of the needle and the cannula being both visible under ultrasonic observation to guide the insertion movement of the needle assembly into a desired location in a body and to confirm the placement of the cannula in the body after removal of the needle.

The instant invention is moreover directed to a needle cannula arrangement comprising an echogenic cannula having a distal end and a coaxial bore, a needle having a sharp tip for insertion into a body removably inserted into the coaxial bore, the needle including at least one echogenic feature at or proximate to the tip, wherein when the needle is fully inserted into the cannula, the tip of the needle is exposed so that the tip of the needle and the cannula are both visible under ultrasound observation when the needle cannula arrangement is placed into a body, the tip guides the insertion movement of the arrangement in the body and the cannula confirms the placement thereof in the body after the removal of the needle.

BRIEF DESCRIPTION OF THE FIGURES

The present invention will become apparent and the invention itself will be best understood with reference to the following description of the present invention taken in conjunction with the accompanying drawings, wherein:

FIG. 1 is an exemplar embodiment of the needle of the instant invention;

FIG. 2 is an enlarged view of the distal portion of the needle of FIG. 1;

FIG. 3 is a cross-sectional view of a section of an exemplar groove of the needle of the instant invention;

FIG. 4 is a cross-sectional view of the exemplar groove showing its neutral position and its "tilted" angle position;

FIG. 5A shows the patient end of the exemplar needle shown in FIG. 1;

FIG. 5B is an enlarged view of a portion of the exemplar needle of FIG. 5A showing crisscrossing spiral grooves;

FIG. 8 is an illustration showing an echogenic needle and an echogenic cannula that are parts of a needle assembly embodiment;

FIG. 9 is an illustration of the needle assembly embodiment where the echogenic needle and the echogenic cannula of FIG. 8 are mounted to each other with the tip of the echogenic needle exposed from the distal end of the cannula; and FIGS. 10A and 10B are enlarged cross sectional views of different sections of the needle assembly embodiment of FIG. 9.

DETAILED DESCRIPTION OF THE INVENTION

Figure 6A:
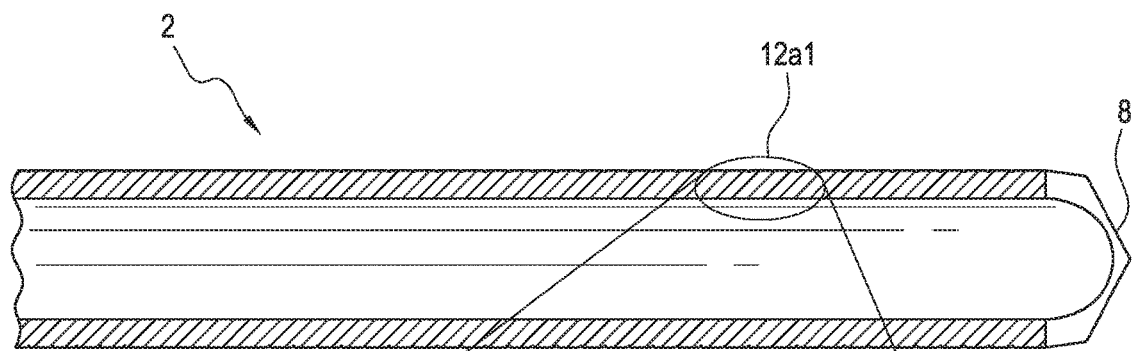
FIG. 6A is a cross-sectional view of a distal or patient end of an exemplar embodiment needle.

An exemplar embodiment of the needle used, for example for peripheral nerve block procedures, is shown in FIG. 1. As shown, needle 2 has a shaft 4 that extends along a longitudinal axis 6 having a distal or patient end 8 including a sharp bevel tip and a proximal end 10. For ease of illustration, the proximal end 10 of needle 2 has been truncated in FIG. 1. The section of the needle that is adjacent to patient end 8 is designated distal portion 12, although it should be appreciated that the demarcation of distal portion 12 as shown in FIG. 1 is for discussion only. Beyond distal portion 12 there are a number of markings 14 along the shaft of the needle to show the length, or the depth of the needle, as the needle is inserted into the subject, or patient. There are two sections 12a and 12b at the distal portion that are better illustrated in the enlarged distal portion view of the needle in FIG. 2.

As shown in FIG. 2, sections 12a and 12b each are formed with crisscrossing spiral grooves that are also shown in FIG. 5B. With reference to FIGS. 2, 5A and 5B, one spiral groove 16a is formed on the outer circumferential wall of needle shaft 4 in one direction, for example a clockwise direction, while an other spiral groove 16b crisscrosses groove 16a in an other direction, for example a counter-clockwise direction. For ease of reference, the respective grooves 16a and 16b spiral about the outer circumferential wall of needle shaft 4 may be referenced with respect to the sharp bevel tip at patient end 8 of the needle. Thus, for the discussion herein below, groove 16a may be considered to be a spiral groove that is formed on the outer circumferential wall of needle shaft 4 in a clockwise direction relative to needle tip 8, while groove 16b spirally wounds about the outer circumferential wall of needle shaft 4 in a counter-clockwise direction relative to needle tip 8. The two spiral grooves crisscross each other in the manner as shown in FIGS. 2, 5A and 5B.

As best shown in FIG. 2, there is a non-groove section 18 that separates grooved sections 12a and 12b at the distal portion of the exemplar embodiment needle. Although two grooved sections are shown in FIGS. 1 and 2, it should be appreciated that a plurality of more than two groove sections may also be formed along the needle away from its patient end.

The configuration of the groove of the needle is illustrated in FIGS. 3-4 and 6A-6C. FIG. 3 shows a cross-section of the needle, for example a portion of section 12a, with directional needle 20 referencing the proximal end of the needle and directional needle 22 referencing the patient end of the needle. As shown in FIG. 3, a number of cross-sections of a groove 16 are shown to have formed on the outer circumferential wall of needle shaft 4, which has a passage 4a extending therethrough along longitudinal axis 6. For the exemplar illustration of FIG. 3, a $\Theta$ angle is shown to be formed between the two walls of the groove, represented by lines 16w1 and 16w2 in FIG. 4. As the walls are orthogonal to each other, the $\Theta$ angle formed between the two walls is assumed to be approximately 90°. Thus, were the spiral groove at the outer surface of the circumferential wall of shaft 4 to be formed to have its walls orthogonal to each other relative to the longitudinal axis of the needle so that the walls have the same length, then each of the walls 16w1 and 16w2 would extend at approximately 45° relative to a plane along the longitudinal axis of shaft 4. This is shown by the dotted lines in FIGS. 4 and 6C, and may be referred to as the neutral position of the groove. For discussion purpose, the length of the walls may also be referred to as the height or distance between the top and bottom, i.e., the valley and apex, of the groove.

The inventors have found that, in use, a clinician usually positions a needle at an angle that facilitates the insertion of the needle into the subject. Thus, were the groove "tilted" at a given angle $\alpha$ toward the proximal end of the needle, an improved reflection of an ultrasound wave directed by an ultrasound transducer towards the needle may be obtained. By empirical studies, it was found that the $\alpha$ angle may range from approximately 5° to 25°, and preferably at 10° relative to the neutral position. Thus, instead of 45° for each of the walls of the V-shaped groove, the "tilted" groove would have its walls, as designed by lines 16w1' and 16w2', shifted together such that wall 16w1' is at a $\beta$ angle relative to the outside walls 4a of the needle shaft. Walls 16w1' and 16w2' remain orthogonal to each other when at the "tilted" position. For the exemplar embodiment where $\alpha$=10°, $\beta$ would be 35°. The depth of the groove may vary anywhere from 0.006 inch to 0.025 inch (0.1524 mm to 0.635 mm). It was further found that the pitch between grooves, as designated by reference number 24 in FIG. 6B, could be reduced to between 0.010 inch and 0.050 inch (0.254 mm to 1.27 mm), and preferably to approximately 0.020 inch (0.508 mm) to improve the pitch density of the needle and thereby its echogeneity. As should be appreciated, the pitch and the depth of the groove as described above are not definitive for all needles but are instead meant to be utilized for needles that have conventionally dimensioned walls, for example a needle having a gauge anywhere between 16 to 24.

Figure 6B:
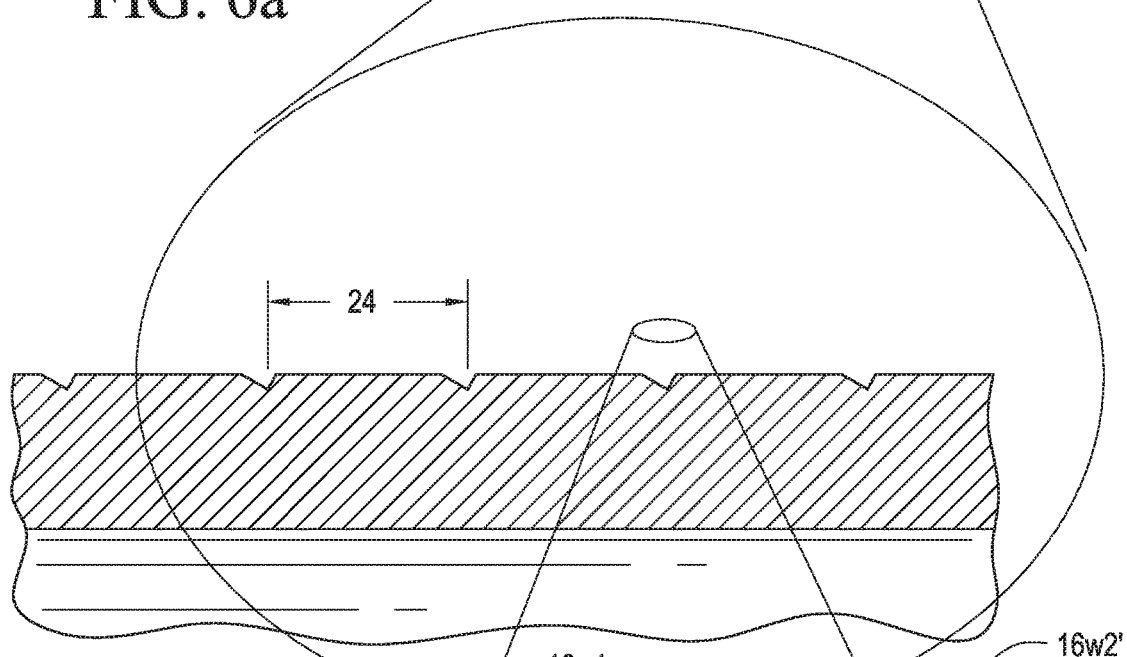
FIG. 6B is an enlarged view of a portion of the wall of the needle of FIG. 6A showing more clearly a number of cross sections of the groove.
Figure 6C:
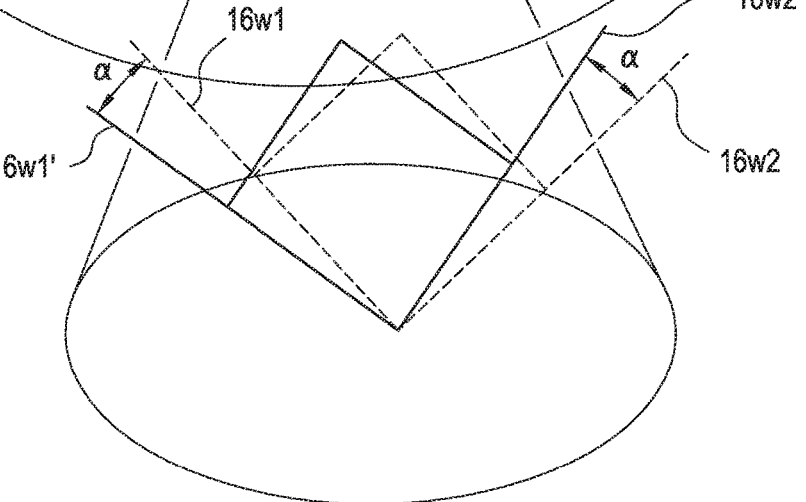
FIG. 6C is an enlarged cross-sectional view showing the two walls of a V-shaped groove at its neutral position and its tilted position.

The configuration of the exemplar embodiment of the echogenic needle of the instant invention is further shown in FIGS. 6A-6C where a portion 12a1 of groove section 12a is enlarged in FIG. 6B to show an enlarged cross-sectional view of a number of V-shaped cross sections of the groove tilted toward the proximal end of the needle as described above. FIG. 6C shows the neutral position (in dotted lines) and the tilt angle position, or simply the tilted position (in solid lines) of the walls of an exemplar cross section of the V-shaped groove.

Figure 7:
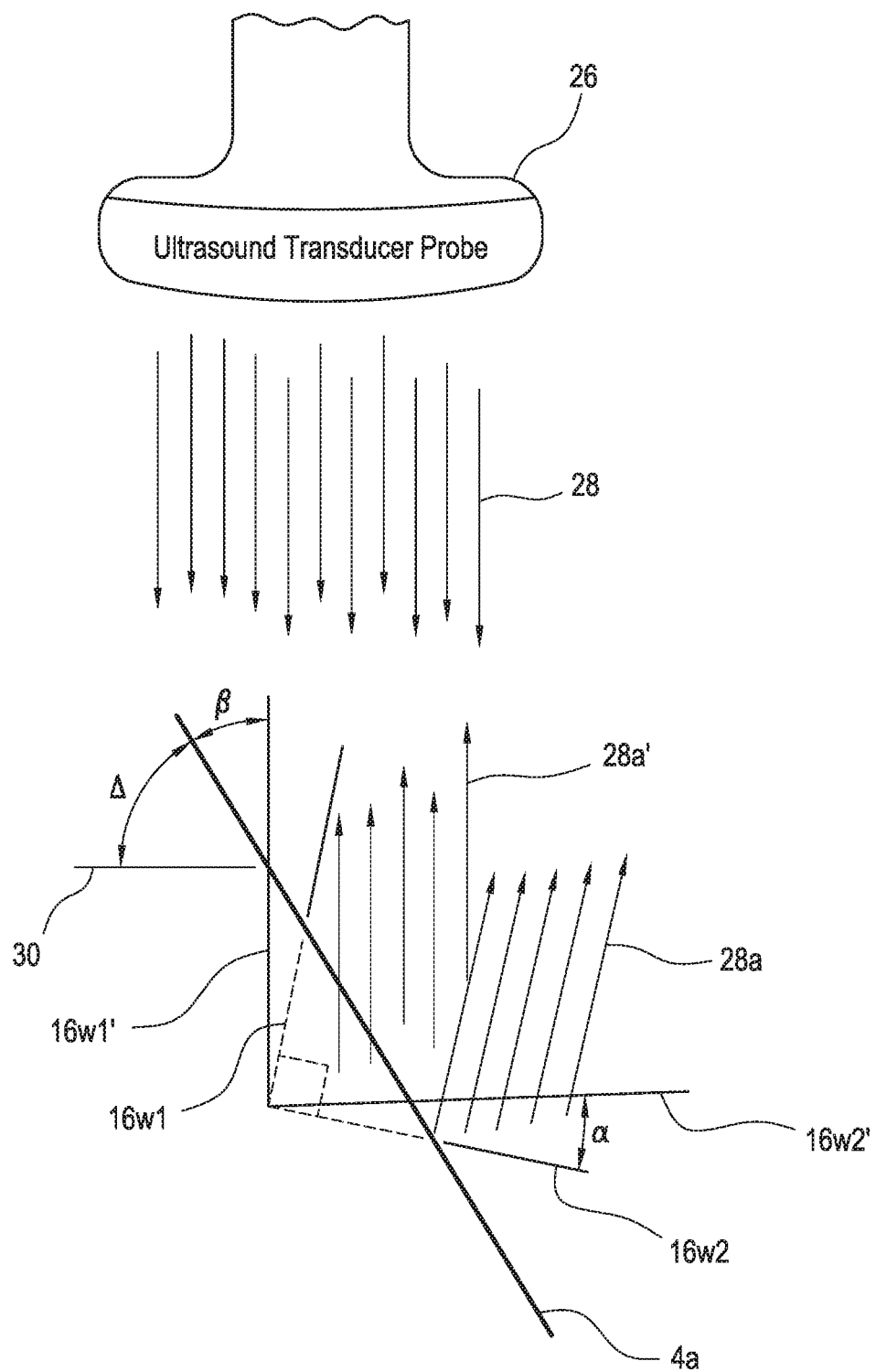
FIG. 7 is an illustration showing an ultrasonic wave emitted from an ultrasonic transducer to the needle, and the reflection of the ultrasound wave back to the transducer by the groove at the neutral position and at the tilt angle position.

FIG. 7 is an illustration showing the difference in the reflection of the ultrasound wave emitted by an ultrasound transducer toward the exemplar embodiment needle. For ease of discussion, the exemplar needle of FIG. 7 is assumed to have only one spiral groove. As shown, the transmitter of ultrasound transducer probe 26 emits an ultrasound wave 28 toward needle shaft 4, represented by line 4a, which is presumably being inserted into a subject. Thus, needle 4 is at an insertion angle $\Delta$ with reference to a plane 30 that is assumed to be in parallel to the plane at the output surface of transducer 26. From empirical studies, it was found that $\Delta$ in most instances is between 50° and 60°, and preferably at approximately 55°. Thus, were the spiral grooves formed in its neutral position, the ultrasound wave 28 would be reflected as a return ultrasound wave, represented by lines 28a, in a direction that angles away, or offsets from ultrasound transducer 26. However, it was determined that with the V-shaped groove at the tilt angle $\alpha$, the ultrasound wave 28 is reflected as ultrasound wave 28a' in a substantially reverse direction (approximately at 180°) back to transducer 26, presumably to its receiver. Thus, an improved reflection view of the exemplar embodiment needle may be gleaned under ultrasound or radiographic imaging by tilting the groove at an angle $\alpha$.

As discussed above, with the exemplar illustration of FIG. 7, it was determined that were the spiral grooves formed at their respective neutral positions, the ultrasound wave 28 would be reflected as a return ultrasound wave, represented by lines 28a, in a direction that angles away, or offset from ultrasound transducer 26. However, from additional empirical studies, it has been determined that were the crisscrossing spiral grooves formed on a needle with their corresponding respective walls orthogonal to the longitudinal axis of the needle but with the pitch density for each of the spiral grooves increased more than as discussed above, an improved and acceptable reflective image of the echogenic portion(s) of the needle under ultrasound imaging can nonetheless be obtained. In other words, spiral grooves formed in the neutral position relative to the longitudinal axis of the needle with a predetermined increased pitch density would provide an improved reflective image of the echogenic portion(s) of the needle, similar to the needle embodiment with the tilted grooves as discussed above.

The neutral positioned spiral grooves are represented by the dotted wall lines 16w1 and 16w2 in FIGS. 4 and 6C. Due to those spiral grooves being formed at the neutral position and orthogonal to each other, their walls, for example 16w1 and 16w2, have substantially the same length or height. The pitch, or the groove width, between the walls of each of the grooves, designated by 24 in FIG. 6, was determined to have a range of approximately 0.001 inch to 0.003 inch (0.025 mm to 0.075 mm), and preferably at approximately 0.0021 inch (0.053 mm). The desired groove depth was determined to be in the range of approximately 0.0006 inch to 0.0010 inch (0.015 mm to 0.025 mm). As should be appreciated, the depth and pitch of the groove may be interrelated, as the change in the value of one may cause a change in the value of the other.

With the combination of clockwise and counter-clockwise spiral wound grooves, and with each of the grooves having a preferable pitch of approximately 0.02 inch (0.508 mm) for the tilted echogenic needle embodiment, an echogenic needle with improved echogeneity results. So, too, an improved echogenic needle adapted to provide improved echogeneity results may be achieved with non-tilted crisscrossing clockwise and counter-clockwise spiral grooves each having an increased pitch density or groove width having a range of 0.001 inch to 0.003 inch (0.025 mm to 0.075 mm), and preferably of approximately 0.0021 inch (0.053 mm). It should be appreciated that instead of a V-shaped groove, each of the grooves may be U-shaped or trapezoidal-shaped, so long as the walls of the groove are made to be substantially orthogonal to each other. Furthermore, one of the crisscrossing grooves may have a V-shape while the other groove may have a U-shape or some other shape including trapezoidal that clearly defines the orthogonal walls of the groove.

Although not disclosed above, it should be appreciated that the proximal end of the needle may be fixedly bonded or connected to a needle hub, so that the needle may be fluidly coupled to a medicament or fluid store, such as a syringe or a pump, to infuse medicament or fluid to the patient once the needle has been inserted into and appropriately positioned within the patient. The respective connectors of the needle hub and the fluid store may be configured to have complementary features or configurations that allow only those connectors to be coupled to each other, i.e., each of those connectors is not connectable to a counterpart conventional luer connector. Moreover, before use, the needle may be protected by a sleeve to prevent contamination and for shipping purposes. To prevent coring of the needle, a stylet may be concentrically fitted into the through passage of the needle when the needle is inserted into the patient, and removed thereafter.

The forming of the spiral grooves onto the outer circumferential wall of the needle shaft may be accomplished in substantially the same manner as is done for the above-noted Wallace Amniocentesis Needles. In the alternative, the spiral grooves may be formed substantially in accordance with the disclosure of JP2000051219, which was assigned to the assignee of the instant invention. In brief, the '219 publication discloses an edge of a spinning wheel is used to form a groove on a catheter that rotatably moves along a longitudinal direction relative to the wheel.

With reference to FIG. 8, an inventive echogenic needle assembly embodiment is shown to include an echogenic needle assembly 32 that has an echogenic feature as described above in combination with an echogenic cannula assembly 42 to form the echogenic needle assembly. For this embodiment, it should be appreciated that cannula 44 of the echogenic cannula assembly 42 may also be a solid or hollow shaft or a catheter. As shown, needle assembly 32 has a needle shaft or simply needle 32a that extends to a patient end 34 that has a bevel sharp tip 34a. At tip 34a or proximate thereto is an echogenic feature 36 such as the spiral groove as described above. For ease of discussion, echogenic feature 36 is shown in FIG. 8 to be one spiral groove. However, it should be appreciated that echogenic feature 36 may include the crisscrossing dual grooves as described above. Needle 32a has a shaft body that extends longitudinally from patient end 34 to a needle hub 40 at the non-patient end 38 of needle assembly 32. As shown, needle hub 40 has a first portion 40a to which a non-patient end portion of needle 32a is bondedly attached. There is also a circumferential flange portion 40b rising from first portion 40a that is adapted to frictionally mate with the hub of the cannula assembly 42 as will be described below. Needle hub 40 further has a main body portion 40c and an end connector 40d that enables needle assembly 32 to be connected to a fluid store such as a syringe or a pump so that fluid or medicament can be conveyed longitudinally along needle assembly 32 between non-patient end 38 and the patient end 34 through an aperture that extends longitudinally along the shaft of needle 32a and hub 40, as is well known.

Also shown in FIG. 8, echogenic cannula assembly 42 may comprise a longitudinal shaft, catheter or sleeve, or simply cannula 44 that defines an axial bore 46 that has a distal end 48 and a proximal end 50. At proximal end 50 there is a cannula hub 52. Hub 52, as shown in the cross-sectional view of FIG. 8, is cone shaped such that its internal passage 52a is adapted to accept portion 40a of needle hub 40. Needle hub 40 and cannula hub 52 are frictionally held to each other by the frictional engagement between the inner wall of passage 52a of cannula hub 52 and the circumferential flange 40b of needle hub 40. The outer circumferential wall of cannula 44 is smooth while a plurality of bubbles 53 are formed in the body of cannula 44. The formations of the bubbles in the cannula 44 may be achieved in the same manner as disclosed in U.S. Pat. No. 8,092,390 and the above discussed U.S. Pat. No. 8,398,596, both assigned to the assignee of the instant application. The disclosures of the '390 and '596 patents are incorporated by reference herein. As disclosed in the '390 patent, during the extrusion of a medico-surgical device such as a cannula, the formation of the bubbles in the device is achieved by incorporating a gas into the wall of the device such as to form gas bubbles through the major part of the thickness of the wall of the device sufficient to increase the visibility of the device under ultrasound observation.

As noted above, the shaft of cannula 44 may be made of metal including sintered metal having gas interstices so that bubbles may be formed along the cannula, or may be made from a flexible plastic material such as PEBA, nylon, PVC, polyethylene, polyprophelene, polyester or polyurethane to which a foaming agent is added to form gas interstices in the form of gas bubbles 53 along its entire length, or at least one portion thereof. As described in the above incorporated by reference '596 patent, the density of the gas bubbles are selected to ensure that the shaft of cannula 44 is echogenic. Typically the gas bubbles 53 may have a size in the range of $0.1\mu$ to $300\mu$, preferably having a size in the range of $1\mu$ to $50\mu$ and most preferably having a range of $5\mu$ to $10\mu$. Other ways of forming the gas bubbles in the cannula are described in the above incorporated by reference patents.

With reference to FIG. 9, needle assembly 32 and cannula assembly 42 are shown to have fully mounted to each other, with needle hub 40 and cannula hub 52 frictionally coupled to each other and needle shaft 32a of needle assembly 32 extending through axial bore 46 of cannula 44. When thus fully mounted, the tip portion of needle shaft 32a extends beyond the distal end 48 of cannula 44. FIG. 10A is an enlarged cross sectional view of circled section A of FIG. 9 exaggeratedly showing the bevel sharp tip 34a of needle shaft 32a and the wall of cannula 44. As shown, the echogenic spiral groove 36 is proximate or close to the sharp bevel tip 34a and extends out from the distal end 48 of cannula 44 so that, under ultrasound observation, the bevel tip 34a and the echogenic feature 36 of needle shaft 32a of needle assembly 32 that extend beyond the distal end 48 of cannula 44 may be readily observed. A portion of cannula 44 encircling a portion of needle shaft 32a, designated by circled section B in FIG. 9, is shown in the enlarged cross sectional view of FIG. 10B. The plurality of gas bubbles 53 in the body of cannula 44 provides echogeneity for cannula 44.

For the needle assembly embodiment shown in FIG. 9, assume cannula 44 is a plastic sheath or catheter having an axial bore through which the shaft of needle 32a of needle assembly 32 extends. In operation, under ultrasound observation, for example using the ultrasound transducer discussed above, when the needle assembly 32 is inserted into the body of the patient, the sharp tip 34a of the needle 32a will make the initial incision into the body, for example a blood vessel of the subject. This is confirmed by the ultrasound reflection of the echogenic tip portion of the needle 32a. As the needle assembly is further inserted into the body, for example the pierced blood vessel, given that the outer circumferential surface of the cannula 44 is smooth, there is less trauma to the patient. The placement of the echogenic cannula 44 inside the body, for example in the blood vessel, along with the tip portion of the needle 32a can then be confirmed under ultrasound observation. Thereafter, needle assembly 32 is removed leaving in place the echogenic cannula 44. The placement of the echogenic cannula 44 minus the echogenic needle 32a could further be confirmed by ultrasound observation. After confirmation, were the cannula (or catheter) to be used to input a medicament or fluid into the patient, a fluid store may have its connector coupled to end connector 40d of the cannula hub, so that a through fluid passage is established between the fluid store and the distal end 48 of the cannula. To withdraw fluid or blood from the patient, a syringe may have its luer connector end connected to end connector 40d of the cannula hub.

In the case that the cannula is used to guide a guidewire into the body of the patient, after confirmation of the positioning of the cannula, the guidewire is threaded through the axial bore of cannula 44. Thereafter, cannula 44 is removed and the additional procedure of inserting a permanent catheter along the guidewire into the patient, as for example a central venous catheter (CVC) for a CVC procedure to infuse drugs for chemotherapy or nutrition, or medicament into an already implanted port in the patient, can be further carried out. The inventive echogenic needle assembly possibly may also be used for percutaneous tracheotomy, where the needle assembly may be used to effect the incision opening at the trachea of a patient under ultrasound observation. After the removal of the needle, a guidewire may be threaded through the cannula into the trachea of the patient. Thereafter, the cannula is removed, the guidewire may be used to guide a dilator to widen the incision opening at the trachea and the subsequent placement of a tracheostomy tube into the trachea of the patient after the removal of the dilator.

Inasmuch as the present invention is subject to many variations, modifications and changes in detail, it is intended that the matter described throughout this specification and shown in the accompanying drawings be interpreted as illustrative only, and not in a limiting sense. Accordingly, it is intended that the invention be limited only by the sprit and scope of the hereto appended claims.

The invention claimed is:
1. A needle assembly, comprising:
an echogenic cannula having an echogenic longitudinal shaft of a given length that is echogenic along the entire given length, the shaft defined by a circumferential wall having an outer wall surface and an inner wall surface defining an axial bore that has a distal end and a proximal end connected to a cannula hub, the outer wall surface and the inner wall surface each are smooth along the entire length of the echogenic cannula; and
a needle having a shaft defining a through passage extending distally from a needle hub having an end connector adapted to be connected to a fluid store such that fluid can be conveyed through the passage of the shaft to a patient end of the needle, the shaft having a longitudinal axis, an outer circumferential wall and a sharp tip at the patient end, the needle having an echogenic feature that includes at least one continuous groove spirally wound about the outer circumferential wall of the shaft from at least adjacent the sharp tip to a predetermined distance away from the sharp tip, the one groove having two walls orthogonal to each other formed onto the outer circumferential wall along the predetermined distance of the shaft such that the orthogonal walls each are formed at an angle ($\alpha$) tilted toward the proximal end of the shaft, one of the walls is formed at an angle ($\beta$) relative to the longitudinal axis of the shaft, the angle ($\beta$) resulting from subtraction of the angle ($\alpha$) from a would be neutral position of the walls wherein the walls each are angled at approximately 45° from the longitudinal axis, the needle adapted to be inserted into a body at an insertion angle ($\Delta$) offset from emitted ultrasound waves by the angle ($\beta$) such that ultrasound waves directed toward the needle are reflected in a reverse direction by at least one of the walls of the groove, the needle slidably extending along the axial bore of the cannula such that the needle hub and the cannula hub are engaged to each other and the sharp tip and at least a portion of the echogenic feature of the needle extend beyond the distal end of the cannula when the needle assembly is to be inserted into the body;
wherein the portion of the echogenic feature that extends beyond the distal end of the cannula and the echogenic cannula are both visible under ultrasonic observation during placement of the needle assembly into the body, the echogenic feature that extends beyond the distal end of the cannula adapted to guide insertion movement of the needle assembly into a desired location in the body, wherein the echogenic cannula is configured to remain in the body after the placement of the needle assembly to the desired location in the body such that the location of the echogenic longitudinal shaft of the cannula in the body is confirmable under ultrasonic observation after the needle is removed from the cannula.
2. The needle assembly of claim 1, wherein the echogenic cannula comprises a plastic tubing and the circumferential wall has a thickness, the plastic tubing having a plurality of bubbles in the circumferential wall along the length of the tubing.

3. The needle assembly of claim 1, wherein the echogenic cannula comprises a plastic tubing having a plurality of bubbles provided in the circumferential wall along the entire length of the plastic tubing.

4. The needle assembly of claim 1, wherein the portion of the echogenic feature is distal of the distal end of the echogenic cannula when the needle hub and the cannula hub are engaged to each other.

5. The needle assembly of claim 1, wherein the needle comprises an other spiral groove, the one and other grooves crisscrossing each other in one direction and an other direction along the outer wall of the needle at or proximate to the tip of the needle, the other groove having walls that are orthogonal to each other and tilted at the angle ($\alpha$) toward the proximal end of the shaft.

6. The needle assembly of claim 1, further comprising:
a stylet adapted to be fitted into the through passage of the needle to prevent coring of the needle when the needle is inserted into the body.

7. A needle cannula arrangement, comprising:
an echogenic cannula having a longitudinal shaft defined by an echogenic circumferential wall along the entire length of the longitudinal shaft that has a distal end and a proximal end connected to a cannula hub such that a fluid passage is established between the cannula hub and the distal end of the cannula, the shaft having a smooth outer wall surface and a smooth inner wall surface along the entire length of the shaft, the smooth inner wall surface defining a coaxial bore along the shaft; and
a needle having a longitudinal axis, a sharp distal tip for insertion into a body and a proximal end extending from a needle hub, the needle hub having an end connector adapted to be connected to a fluid store such that fluid can be conveyed from the fluid store to a patient end of the needle, the needle having an echogenic feature that includes at least one groove spirally wound about an outer circumferential wall of the needle from at least adjacent the sharp tip to a predetermined distance away from the sharp tip, the one groove having two walls orthogonal to each other formed onto the outer circumferential wall along the predetermined distance of the needle such that the orthogonal walls each are formed at an angle ($\alpha$) tilted toward the proximal end of the needle, one of the walls is formed at an angle ($\beta$) relative to the longitudinal axis, the angle ($\beta$) resulting from subtraction of the angle ($\alpha$) from a would be neutral position of the walls wherein the walls each are angled at approximately 45° from the longitudinal axis, the needle adapted to be inserted into the body at an insertion angle ($\Delta$) offset from emitted ultrasound waves by the angle ($\beta$) such that ultrasound waves directed toward the needle are reflected in a reverse direction by at least one of the walls of the groove, the needle removably inserted into the coaxial bore such that the cannula hub and the needle hub are frictionally engaged and at least a portion of the echogenic feature of the needle is exposed beyond the distal end of the echogenic cannula as an echogenic tip portion, the echogenic tip portion of the needle and the cannula are both visible under ultrasound observation, the echogenic tip portion adapted to be observed under ultrasound to guide movement of the needle and the echogenic cannula into the body, wherein the shaft of the echogenic cannula is observable along its entire length under ultrasound to confirm the placement thereof in the body after the needle is removed from the cannula.

8. The needle cannula arrangement of claim 7, wherein the cannula is a plastic tubing and the circumferential wall has a thickness, the plastic tubing having a plurality of bubbles in the circumferential wall along the length of the tubing.

9. The needle cannula arrangement of claim 7, wherein the echogenic cannula comprises a plastic tubing having a plurality of bubbles provided in the circumferential wall along the entire length of the plastic tubing.

10. The needle cannula arrangement of claim 7, wherein the echogenic feature portion at the distal tip of the needle is distal of the distal end of the echogenic cannula when the needle hub and the cannula hub are engaged to each other.

11. The needle cannula arrangement of claim 7, wherein the echogenic feature of the needle comprises the one groove and an other groove crisscrossing each other in one direction and an other direction along the outer circumferential wall of the needle at or proximate to the tip of the needle, the other groove having walls that are orthogonal to each other and tilted at the angle ($\alpha$) toward the proximal end of the shaft.

12. The needle cannula arrangement of claim 7, wherein the needle has a through passage, the arrangement further comprising:
a stylet adapted to be fitted into the through passage of the needle to prevent coring of the needle when the needle is inserted into the body.

* * * * *